United States Patent
Ouchi et al.

(10) Patent No.: US 7,557,588 B2
(45) Date of Patent: Jul. 7, 2009

(54) METHOD AND APPARATUS FOR INSPECTING AN OBJECT USING TERAHERTZ ELECTROMAGNETIC WAVE

(75) Inventors: Toshihiko Ouchi, Sagamihara (JP); Shintaro Kasai, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 190 days.

(21) Appl. No.: 11/727,588

(22) Filed: Mar. 27, 2007

(65) Prior Publication Data

US 2007/0252604 A1 Nov. 1, 2007

(30) Foreign Application Priority Data

Apr. 28, 2006 (JP) .............................. 2006-125670

(51) Int. Cl.
*G01R 27/04* (2006.01)
*G01R 31/302* (2006.01)

(52) U.S. Cl. ...................................... 324/637; 324/750

(58) Field of Classification Search ................. 324/637
See application file for complete search history.

(56) References Cited

U.S. PATENT DOCUMENTS

| 5,929,644 | A * | 7/1999 | Sokolov ..................... 324/750 |
| 6,297,489 | B1 * | 10/2001 | Suyama et al. ............... 250/207 |
| 7,248,995 | B2 | 7/2007 | Itsuji et al. |
| 2001/0019271 | A1 * | 9/2001 | Scott et al. .................. 324/637 |
| 2004/0058339 | A1 | 3/2004 | Nagel et al. |
| 2004/0066207 | A1 * | 4/2004 | Bottoms et al. ............. 324/754 |
| 2004/0155665 | A1 * | 8/2004 | Arnone et al. ............... 324/644 |
| 2005/0156607 | A1 * | 7/2005 | Okamura ..................... 324/639 |
| 2006/0085160 | A1 | 4/2006 | Ouchi |
| 2006/0188398 | A1 | 8/2006 | Yano et al. |
| 2006/0197021 | A1 | 9/2006 | Ouchi |

(Continued)

FOREIGN PATENT DOCUMENTS

DE          102 57 225 B3       4/2004

(Continued)

OTHER PUBLICATIONS

U.S. Appl. No. 11/632,958, 371(c) filed Jan. 19, 2007, Applicant: Toshihiko Ouchi.

(Continued)

*Primary Examiner*—Vincent Q Nguyen
*Assistant Examiner*—Jeff Natalini
(74) *Attorney, Agent, or Firm*—Fitzpatrick, Cella, Harper & Scinto

(57) ABSTRACT

An inspection apparatus including a transmission line for propagating an electromagnetic wave; an electromagnetic wave supply unit for supplying a terahertz wave to the transmission line; an electromagnetic wave detection unit for detecting the terahertz wave from the transmission line; a conductive region; an inspection object supply unit; and a deposition unit. The conductive region is arranged at a site including at least a part of the range to which an electric field distribution of the electromagnetic wave propagating through the transmission line extends. The inspection object supply unit holds and supplies the inspection object to the outside, and the deposition unit deposits the inspection object selectively on the conductive region by electrostatic force. The electromagnetic wave supplied from the electromagnetic wave supply unit and propagated through the transmission line is detected by the electromagnetic wave detection unit to obtain information on the inspection object.

3 Claims, 5 Drawing Sheets

U.S. PATENT DOCUMENTS

| | | |
|---|---|---|
| 2006/0214176 A1 | 9/2006 | Ouchi et al. |
| 2006/0227340 A1 | 10/2006 | Shioda et al. |
| 2006/0244629 A1 | 11/2006 | Miyazaki et al. |
| 2007/0030115 A1 | 2/2007 | Itsuji et al. |
| 2007/0195921 A1 | 8/2007 | Ouchi et al. |
| 2007/0215808 A1 | 9/2007 | Sekiguchi et al. |
| 2007/0229094 A1 | 10/2007 | Kasai et al. |
| 2007/0235718 A1 | 10/2007 | Kasai et al. |
| 2008/0048792 A1 | 2/2008 | Ouchi et al. |
| 2008/0231384 A1 | 9/2008 | Sekiguchi et al. ........... 331/115 |
| 2008/0314152 A1 | 12/2008 | Ouchi .................... 73/597 |

FOREIGN PATENT DOCUMENTS

| | | | |
|---|---|---|---|
| WO | WO 2005/001505 | * | 1/2005 |
| WO | 2006/011636 A1 | | 2/2006 |

OTHER PUBLICATIONS

U.S. Appl. No. 10/857,261, International Filing Date: Mar. 27, 2006, Applicants: Ryota Sekiguchi, et al.

M. Nagel, et al., "Integrated planar terahertz resonators for femtomolar sensitivity label-free detection of DNA hybridization", Applied Optics, vol. 41, No. 10, Apr. 2002, pp. 2074-2078.

Nagel M. et al., "Integrated Planar Terahertz Resonators For Femtomolar Sensitivity Label-Free Detection DNA Hybridization" Applied Optics, Optical Society Of America. vol. 41, No. 10, (Apr. 1, 2002), pp. 2074-2078.

Stewing F. et al., "A New Class Of Improved-Efficiency THZ Filters For On-Chip Detection Of Biomaterials", Microwave and Optical technology letters, John Wiley, New York, NY. vol. 41, No. 2, (Apr. 20, 2004), pp. 79-82.

Nagel M. et al., "Integrated THz technology for label-free genetic diagnostics" Applied Physics Letters, American Institute Of Physics, Melville, NY, vol. 80, No. 1, (Jan. 7, 2002), pp. 154-156.

Baras T. et al., "Design consideration for on-chip THz analysis of biomoleculees" Terahertz Electronics Proceedings, 2002. IEEE Tenth International Conference, Piscataway, NJ. (Sep. 9, 2002), pp. 77-80.

Baras T. et al., "On-Chip THZ Detection Of Biomaterials: A Numerical Study" Journal Of Biological Physics, KluwerAcademic Publishers, Dordrecht, Netherlands, vol. 29, No. 2/3, (2003), pp. 187-194.

U.S. Appl. No. 10/587,261, International Filing Date: Mar. 27, 2006, Applicants: Ryota Sekiguchi, et al.

* cited by examiner

METHOD AND APPARATUS FOR INSPECTING AN OBJECT USING TERAHERTZ ELECTROMAGNETIC WAVE

BACKGROUND OF THE INVENTION

1. Field of the Invention

The present invention relates to an inspection apparatus and an inspection method for obtaining information (physical properties, identification, concentration, presence or absence, and the like) of an inspection object by using an electromagnetic wave referred to as a so-called millimeter wave or terahertz wave of frequencies between 30 GHz and 30 THz (referred to as "terahertz wave" in this specification).

2. Description of the Related Art

In recent years, the technical development using a terahertz wave has been eagerly advanced. In particular, photon energy of the terahertz wave is comparable to energy of skeletal vibration of molecules or of interaction between the molecules. A technique using this terahertz wave is used to analyze a substance by using a spectrum and the like obtained by a spectroscopic method.

Under such technical situation, there is proposed a technique of analyzing DNA by utilizing the condition that terahertz wave propagation properties of a transmission line change when the terahertz wave transmission line is produced on a substrate, and a DNA water solution is dropped onto the transmission line and dried (APPLIED OPTICS/Vol. 41, No. 10, 2002, pp. 2074). This technique is studied because, by propagating the terahertz wave through the transmission line, it is possible to obtain an inspection apparatus which is reduced in size, is strong against an external environmental change, and can detect an inspection object of a very small amount. Further, this proposal indicates that, by utilizing the fact that a dielectric constant for the terahertz wave is different between a single chain and double chain of DNA, it is possible to inspect whether the DNA is made of the single chain or the double chain, in accordance with the difference of the terahertz wave propagation properties.

The configuration of this proposal has: a semiconductor thin film that functions as a photoconductive element; and a small functional device having transmission lines integrated on one substrate for propagating a generated electromagnetic wave. FIG. 7 shows a plan view thereof. In this configuration, there is provided a structure 164 obtained by transferring only a thin film of an epitaxial layer of a photoconductive element made of LT-GaAs onto a part of high frequency transmission lines 165 and 163 formed on a substrate 160. In this configuration, the structure 164 has such a structure that a micro strip line is formed on the Si substrate 160 so as to sandwich an insulator resin therebetween, a gap is generated in a part of the line, and the LT-GaAS thin film is arranged only below the gap. Driving is carried out such that a laser beam is emitted from a surface side of the substrate 160 through spatial propagation to gaps of metal lines 161 and 165, and the generated terahertz electromagnetic wave is propagated through the lines. On the transmission line, when an inspection object 167 to be examined is coated on a filter region 166 as a resonance structure, an EO crystal is used to detect a change in propagation state from a part 162. Thus, the physical properties of the inspection object 167 can be examined.

As mentioned above, the terahertz wave is used to determine optical properties, such as absorption coefficient and complex refractive index of a substance, from its change in the propagation state. Consequently, the analysis, detection, and identification of a substance can be executed. However, the method of APPLIED OPTICS, Vol. 41, No. 10, 2002, pp. 2074 does not use a special unit to drop the inspection object onto the transmission line with high controllability. Thus, it is not easy to drop the inspection object with high controllability in terms of the quantity and the position. That is, since the dropped liquid inspection object is apt to flow and spread, it is not easy to suitably control the position and amount of the inspection object for the transmission line.

SUMMARY OF THE INVENTION

An inspection apparatus of the present invention includes: a transmission line for propagating an electromagnetic wave; an electromagnetic wave supply unit for supplying a terahertz wave to the transmission line; an electromagnetic wave detection unit for detecting the terahertz wave from the transmission line; a conductive region; an inspection object supply unit; and a deposition unit. In this case, the conductive region is arranged at a site that includes at least a part of a range to which an electric field distribution of the electromagnetic wave propagating through the transmission line extends. The inspection object supply unit holds an inspection object and supplies the inspection object to the outside, and the deposition unit deposits the inspection object, which is supplied from the inspection object supply unit, selectively on the conductive region by an electrostatic force. Consequently, the electromagnetic wave that is supplied from the electromagnetic wave supply unit and propagated through the transmission line is detected by the electromagnetic wave detection unit to obtain the information of the inspection object.

Further, in view of the above-mentioned problems, an inspection method of the present invention includes the steps of detecting a terahertz wave propagated through a transmission line, and obtaining the information of an inspection object deposited on a conductive region located in a site including at least a part of a range to which the electric field distribution of an electromagnetic wave propagating through the transmission line extends. In this case, the inspection object is supplied from an inspection object supply unit for holding the inspection object and supplying the inspection object to the outside, a voltage is applied between the conductive region and an inspection object holding portion of the inspection object supply unit to generate electric field, and the supplied inspection object is guided by electrostatic force and selectively deposited on the conductive region.

According to the inspection apparatus and method of the present invention, since the supplied inspection object is selectively deposited on the conductive region by electrostatic force, the supply amount and deposition position of the inspection object to a desirable region can be adjusted at a relatively good controllability. Thus, even the quantitative obtainment (detection, inspection, measurement or the like) of the information of the inspection object can be carried out at a good reproducibility.

Further features of the present invention will become apparent from the following description of exemplary examples with reference to the attached drawings.

DESCRIPTION OF THE EMBODIMENTS

Figure 1:
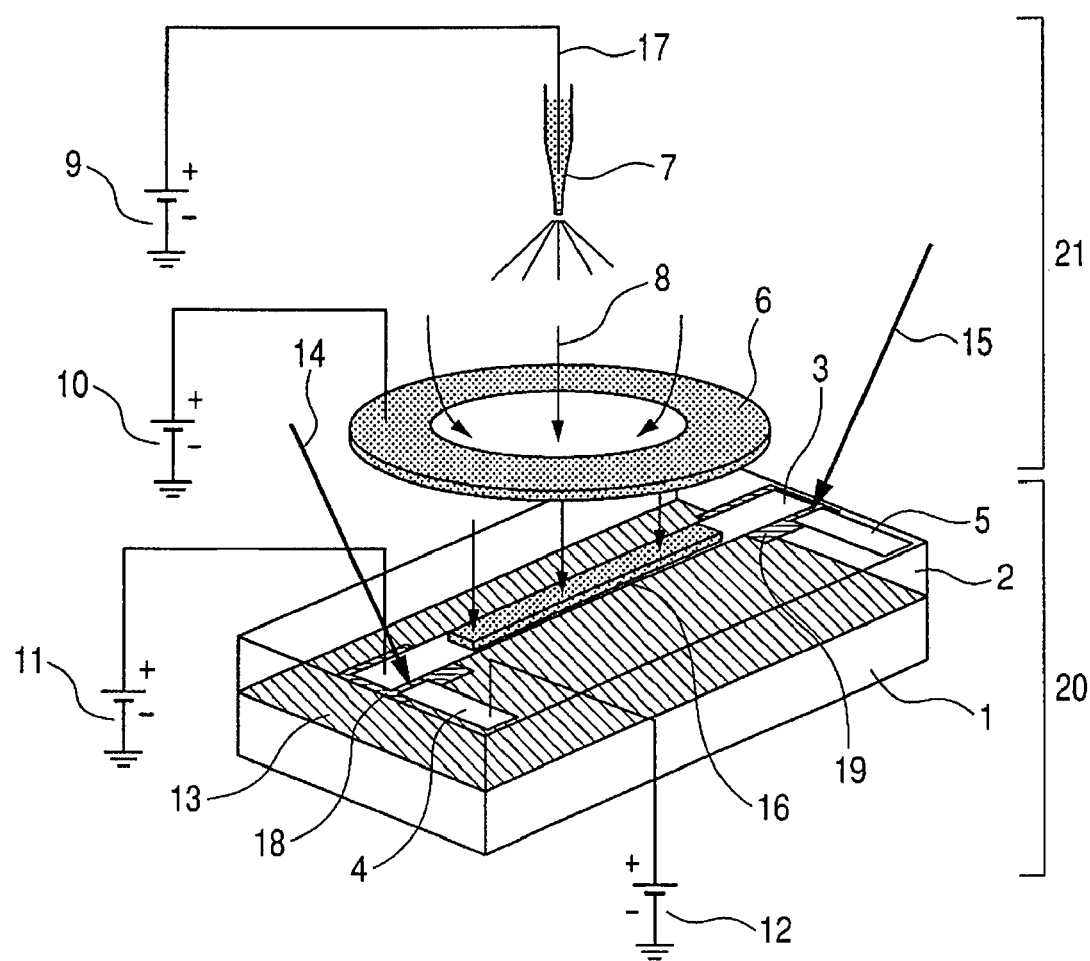
FIG. 1 is a perspective view of an inspection apparatus that uses a transmission line (micro strip) type sensor according to an embodiment and a first example of the present invention.

The embodiment of the present invention will be described below. An inspection apparatus of the embodiment of the present invention has: a terahertz wave supply portion, a terahertz wave detection portion, coupling portions for coupling a terahertz wave to the terahertz wave supply portion and the terahertz wave detection portion, and a transmission line for propagating the terahertz wave between the coupling portions. The terahertz wave supply portion and the coupling portion constitute the electromagnetic wave supply unit, and the terahertz wave detection portion and the coupling portion constitute the electromagnetic wave detection unit. Although this is repeatedly described, the term "terahertz wave" herein represents electromagnetic waves included in a wavelength range between 30 GHz and 30 THz. Further, this inspection apparatus further has: an inspection object supply unit for supplying an inspection object by causing the inspection object to fly in space (outside); and a deposition unit for depositing the inspection object selectively on only a conductive region (for example, a metal portion or metal region serving as a signal line of the transmission line may be installed) while converging the inspection object with electrostatic force. With such configuration, for example, with regard to the terahertz wave that is supplied from the electromagnetic wave supply portion and propagated via the electromagnetic wave coupling portion through the transmission line, the change in the propagation state caused by the deposition amount and component of the inspection object is obtained by the electromagnetic wave detection portion. Consequently, the inspection object can be inspected and detected.

In this embodiment, the deposition unit has a unit for generating an electric field by applying a voltage between the inspection object holding portion of the inspection object supply unit and the conductive region, and consequently while converging the inspection object with the electrostatic force, the inspection object is selectively deposited only on the conductive region. Further, in order to converge the supplying or flying state of the inspection object to the conductive region, a collimator electrode to which a proper voltage is applied in the supply state of the inspection object may be further installed between the inspection object holding portion of the inspection object supply unit and the conductive region. Further, in order to control the drying state when the inspection object is deposited on the conductive region, a humidity control unit for adjusting the humidities of the space to which the inspection object is supplied and the space surrounding the conductive region may be further installed.

In order to supply the inspection object while causing the inspection object to fly in space, the following unit may be employed. It is possible to use a unit for applying a kV-order high electric field between a capillary that is a thin tubular holder for holding the inspection object in a liquid state and a substrate on which the inspection object is stuck. Further, it is possible to preferably use a unit for discharging the inspection object as a micro droplet by giving a supersonic wave to the capillary or by ejecting the liquid inspection object through a micro aperture by heating or using a piezo-effect like an ink jet system. Moreover, when the electrostatic field is applied between the capillary and the conductive region on which the inspection object is desired to be deposited, the inspection object can be selectively deposited by the electrostatic force. At this time, when in the vicinity of the substrate to be stuck, a ring-shaped electrode is installed being provided with a dielectric cover to apply an intermediate electric field, it can act as a collimator electrode for suitably regulating the flying of the inspection object.

In a transmission line type sensor, a signal line is made of metal, and its periphery is made of dielectric. Thus, an inspection object is deposited on a signal line portion as the conductive region, namely, the region having a high sensibility (the region where the propagated terahertz wave and the inspection object strongly interact with each other) and additionally only on a specific region. At this time, with an elapse of time, the deposition of the inspection object is changed only in the height direction. Hence, the quantitative evaluation can be attained.

One example of the present invention will be described below in detail by using FIG. 1. FIG. 1 illustrates a transmission line type terahertz sensor chip 20 of a micro strip type and an inspection object coating apparatus 21. In this case, as the inspection object coating method, an electrospray deposition method (refer to "Japanese Patent Application Laid-Open No. 2001-281252") that can apply the inspection object in a substantially dry state selectively on a sensor portion of the transmission line, namely, a part of a signal line 3 of the transmission line for the terahertz wave propagation is preferably used. In this case, the solution in which the inspection object is dissolved is contained in a capillary 7, and a power source 11 for setting the signal line 3 to a predetermined potential and a power source 9 connected to a capillary electrode 17 in the solution inside the capillary 7 are controlled. Consequently, the electric field is applied between the signal line 3 and the capillary electrode 17, and the solution is atomized in the form of spray. At this time, the atomizing of the solution is controlled so as not to be diffused more than necessary by a power source 10 connected to an annular collimator electrode 6. In this way, while a liquid droplet in which the inspection object molecules are dissolved is running as illustrated by an arrow indicated by reference numeral 8, the liquid is evaporated and dried, and the substantially dried solute portion is selectively stuck only on the signal line 3 that is a metal portion, and deposited as indicated by reference numeral 16. The liquid droplet in which the inspection object molecules are dissolved has a large surface area as compared with its volume. Thus, the evaporation of the liquid is promoted during the flying, and the liquid is dried.

At this time, a dielectric 2 that is formed on a ground plane 13 on a substrate 1 and constitutes a micro strip line serving as the transmission line has an insulating property. Thus, this dielectric 2 takes the role of a mask against the electrospray, and hence the inspection object is hardly stuck thereon. For this reason, as small an amount of inspection object as possible can be applied on the sensor portion with good controllability and efficiency. Further, when it is stuck, it is substantially dried. Thus, while the measurement of the terahertz wave and the coating of the inspection object are executed in parallel at the same time, it is possible to get the temporal change of the propagation state of the terahertz wave propagating through the transmission line. Moreover, the deposition region of the inspection object can be defined by the signal line 3 and the collimator electrode 6. Hence, as for the deposition amount of the inspection object with respect to time, only the thickness direction is a parameter, and it is possible even for the quantitative measurement of the inspection object. In order to control the drying state, a mechanism for holding the entire apparatus at a constant temperature and a constant humidity may be added.

While another constituent portion of the transmission line type terahertz sensor chip 20 in this embodiment is described, the operation method of the terahertz sensor chip 20 is described. In FIG. 1, a femto second laser beam 14 is emitted to a gap portion between the signal line 3 and a side electrode 4 which are formed on a GaAs thin film 18 on the substrate 1. At this time, when the power source 11 and a power source 12 are so designed as to apply the electric field to the gap portion, this portion functions as a photoconductive switching element, and thus a terahertz pulse is generated and coupled to the signal line 3 and then propagated through the signal line 3. This terahertz wave arrives at a photoconductive switching element comprised of the signal line 3 and a side electrode 5 that is constituted on another GaAs thin film 19 in the same way. A laser beam 15 obtained by splitting the femto second laser beam is synchronously applied to the gap portion of this photoconductive switching element. Thus, the signal of the terahertz wave can be detected as a current. In this case, a signal change that is caused correspondingly to conditions or thickness of an inspection object molecule 16 deposited on the signal line 3 is analyzed, thereby enabling the information of the analysis of the inspection object to be obtained.

Figure 2:
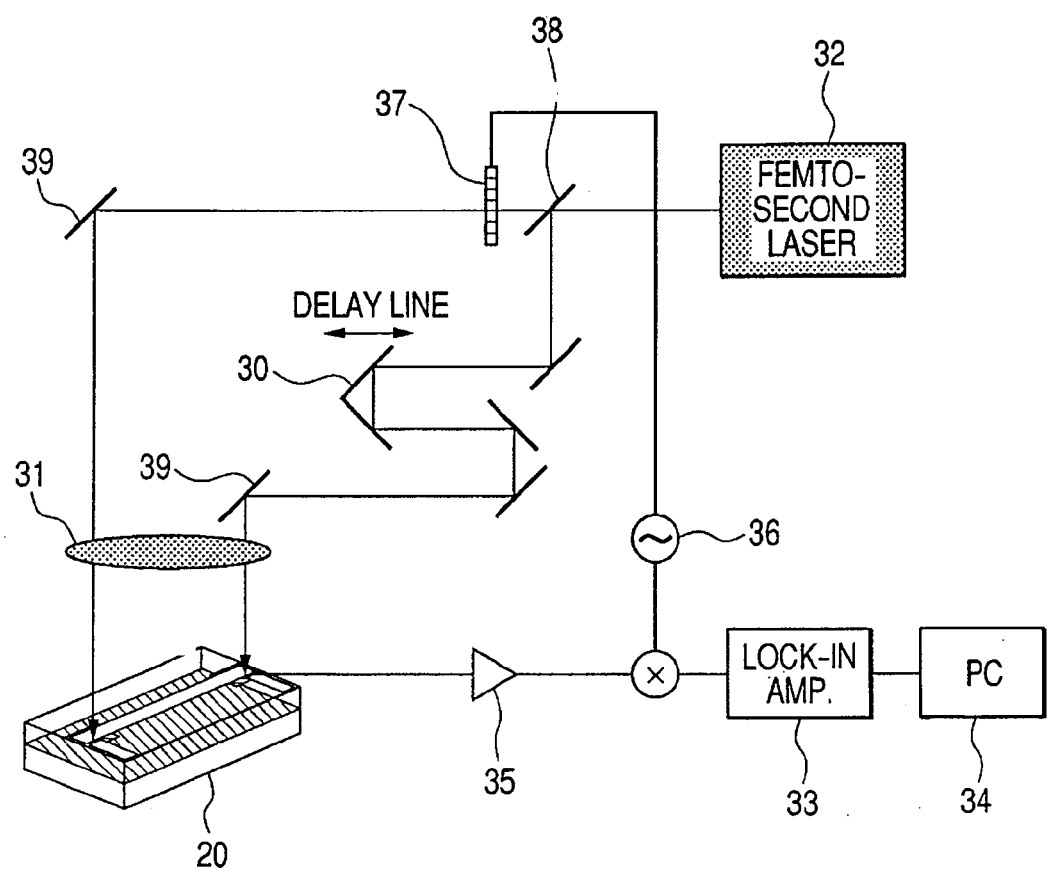
FIG. 2 is a view illustrating an optical arrangement example of the inspection apparatus of the present invention.

The entire apparatus of this embodiment is illustrated in FIG. 2. The light generated from a femto second laser apparatus 32 has a pulse width of 100 fsec and a central wavelength of 800 nm. This light is split into two components by a beam splitter 38. Then, one component is modulated by a chopper 37 and emitted through a mirror 39 and a lens 31 to a terahertz wave generation side gap portion of the sensor chip 20. The chopper 37 is driven in response to a modulation signal from an oscillator 36, and this modulation signal is also sent to a lock-in amplifier 33 which will be described later. The other light is emitted via a delay line 30, similarly through the mirror 39 and the lens 31, to a terahertz wave detection side gap portion of the sensor chip 20. While the delay time is varied by the delay line 30, through an amplifier 35 and the lock-in amplifier 33, a personal computer (PC) 34 analyzes the signal change of the terahertz wave propagated through the transmission line. Hence, the sensing data (information of the inspection object) can be obtained.

At this time, since the deposition amount of the inspection object molecules is increased with the elapse of time, the reaction of the terahertz wave with the inspection object molecule is temporally changed. For the temporal change, a sequential measurement is carried out as mentioned above, and thus the change amount is analyzed, thereby enabling the improvement of the stability and reliability of the inspection object inspection. As a matter of course, after the completion of the deposition of the inspection object, the inspection object may be inspected.

In the above-mentioned embodiment, the electrospray deposition method is used to apply and deposit the inspection object on the target conductive region. However, as the method of converging and depositing the inspection object on the target conductive region, it is possible to use a method of using an ink jet method, a supersonic method, and the like to eject the inspection object, and then using an electrostatic force to draw the inspection object to the target conductive region. In this case, it is necessary to arrange an electrode such as the annular electrode 6 around or near the ejection portion and then apply a voltage thereto and to thereby generate a desirable electric field. However, the energy for ejecting the inspection object from the ejection portion is supplied by a method except for the electric field. Thus, the voltage can be made lower than a voltage applied to the capillary electrode 17.

Further, in the above-mentioned embodiment, the micro strip line is used as the transmission line. However, the structure and shape of the transmission line is not limited to the micro strip line. It is possible to use a strip line, a coplanar strip line (refer to FIG. 6), a coplanar wave guide, a micro coplanar strip line, a slab line, a slot line, and the like. Further, although a part of the signal line of the transmission line is used as the conductive region on which the inspection object is deposited, a conductive region separately formed near the transmission line may be used. However, this conductive region is required to be formed in a range to which the electric field distribution of the electromagnetic wave propagating through the transmission line extends. For example, if the conductive region is formed in a site that includes at least a region having an electric field of $1/e^2$ or more of the peak value of the electric field distribution of the propagation electromagnetic wave, the inspection object and the electromagnetic wave effectively interact with each other, which can have effective influence on the electromagnetic wave propagating through the transmission line. In this case, a unit for controlling a potential of the conductive region such as a different electrode may be provided. It is noted that the propagation property of the transmission line is designed including the conductive region.

According to the above-mentioned embodiment, the inspection substance in the liquid inspection object of a desirable amount is applied on the transmission line in a constant amount every time, and the inspection substance can be measured in a dry state immediately after application thereof. Thus, the quantitative reliable measurement can be attained. That is, in the case of the deposition by the method described above, a solute is stuck on the signal line in such a state that a solvent is substantially evaporated while micro droplets of the inspection substance are flying in a case of a solution. Thus, immediately after the deposition, the measurement through the terahertz wave can be executed. By using this condition, the signal of the terahertz wave is always monitored, and with the elapse of time for the deposition, the signal change can be also analyzed. In this way, according to the temporal change of the deposition amount of the inspection object onto the conductive region, a plurality of changes of the signal of the detected terahertz wave is obtained continuously or intermittently with respect to the elapse of time, thereby obtaining the information of the inspection object.

The above-described inspection is very effective in a case where high sensibility is especially required or in a case where a drift of a signal magnitude results in a problem. As for this drying state, measurement may be conducted in a half-dry state by controlling the peripheral humidity. Further, when the temporal change is monitored, in a case where it is not changed, namely, where a tendency to cause saturation is observed or where a saturation point can be estimated, the inspection object supply may be stopped, and the inspection object more than necessary is never wastefully used. In this way, when the rate of the change in the signal of the detected terahertz wave with respect to the elapse of time becomes small, or when the rate of the change is estimated to be small, the supply of the inspection object can be stopped.

If an alternating current electric field is superimposed on a mechanism for supplying the inspection object, the deposition rate of the inspection object is modulated. However, if the synchronous detection is performed on this change, it is possible to attain the inspection with high S/N ratios and small influence of the drift. In this way, the information of the inspection object can be also obtained by superimposing the alternating current component on the voltage to be applied to the inspection object holding portion of the inspection object supply means, varying the rate of the deposition onto the conductive region of the inspection object, and then executing the synchronous detection with this variation.

As described above, according to the inspection apparatus and method of this embodiment, an inspection object to be supplied is deposited selectively on the conductive region by electrostatic force. Thus, the supply amount and deposition position of the inspection object can be adjusted with relatively high controllability. Further, liquid droplets of the inspection object are caused to fly and are deposited selectively on only the metal portion serving as the signal line of the transmission line by the electrostatic force, while the inspection object is being converged. Thus, since the inspection object can be applied in the substantially dry state, the inspection object can be immediately measured. Hence, the influence of the drift can be reduced. In this way, when the liquid inspection object is applied, the time for a drying process is not required. In addition, in the case of the comparison with a reference, the influence of the temporal drift can be avoided, thereby attaining the inspection with high precision.

On the contrary, in the case of the method of the APPLIED OPTICS/Vol. 41, No. 10, 2002, pp. 2074, when the liquid inspection object is dropped onto the transmission line substrate or the like and dried, the thickness of the precipitated inspection object is apt to be irregular. Further, in the case of the liquid inspection object, the spreading manner of the droplet is different for each drop. Thus, the interaction volume with the terahertz wave is different every time, so the reproducibility is poor and the quantitative measurement is not easy. For example, if the transmission line is roughly treated prior to the sufficient dry, the droplet flows down. As a result, the interaction volume between the inspection object and the terahertz wave is apt to be changed. Further, in the method of APPLIED OPTICS/Vol. 41, No. 10, 2002, pp. 2074, since the dropped position of the droplet is not constant for each measurement, the reproducibility of the measurement is also poor. Moreover, a certain time is required until the liquid inspection object is dropped and dried. Then, a terahertz analysis apparatus of a transmission line type, which detects a small change by comparison with a reference when there is no inspection object, has a fear of the reduction in the precision, because of the drift of the stationary value and the like.

EXAMPLE

A specific example will be described below. Materials, dimensions, driving conditions, and the like described here are just one example, and they are not limited to those described in the example.

First Example

A first example of the present invention will be described below with reference to FIG. 1. This example has a configuration based on the above-mentioned example.

In this example shown in FIG. 1, the inspection apparatus includes the Si substrate 1, a Ti/Au electrode 13 serving as the ground plane, and a BCB 2 (Brand Name: Benzocyclobutene) as a dielectric. Further, members 18 and 19 are obtained as follows: an LT-GaAs film (having a thickness of 2 μm) is epitaxially grown on the GaAs substrate at a low temperature by using an MBE method, and then the GaAs substrate is removed followed by transferring the film as an optical transmission film. The thickness of the BCB 2 is 3 μm, and the width of the Ti/Au electrode serving as a signal line 3 of the transmission line is 5 μm. Each of the gaps formed between the signal line 3 and the side electrodes 4 and 5 is set to 5 μm.

It is so controlled as to apply a voltage of 10 V to a gap portion on the terahertz wave generation side, in accordance with the potential difference between the power source 11 and the power source 12. The laser beam 14 of 10 mW is applied thereto. On the other hand, the laser beam 15 on the detection side of the terahertz wave is set to exhibit 5 mW. At this time, as the inspection object 16 is deposited on the signal line 3, the temporal waveform of the terahertz wave detected on the detection side is illustrated in the schematic diagram of FIG. 3A. Typically, the half width of a pulse is 6 psec, and with respect to the output of the lock-in amplifier 33, the peak value was about 100 mV, and the S/N was about 1000. The entire constitution of the measuring system at this time is illustrated in FIG. 2, and is structured as described in the above-mentioned example.

In this case, for example, avidin as an inspection object of protein is applied on the signal line 3 by an electrospray deposition method. An avidin aqueous solution (having a concentration of 10 mg/ml) is poured into the capillary 7, and a high voltage of about 3 kV is applied between the capillary electrode 17 and the signal line 3. A voltage of 0.5 kV is applied from the power source 10 to the collimator electrode 6, Teflon (Registered Trademark) (not shown) or the like is provided near or on the electrode 6, and the electrode 6 is shielded such that an excessive amount of the inspection object is not stuck on the electrode 6. The coating speed onto the signal line 3 of the inspection object depends on the concentration of the solution of the inspection object, the application voltage between the capillary electrode 17 and the signal line 3, and the like. At this time, the inspection object is hardly deposited on the BCB 2 except for the signal line 3, because the BCB 2 is an insulator. Thus, the inspection object 16 is selectively applied on the signal line 3 as illustrated in FIG. 1.

Figure 3A:
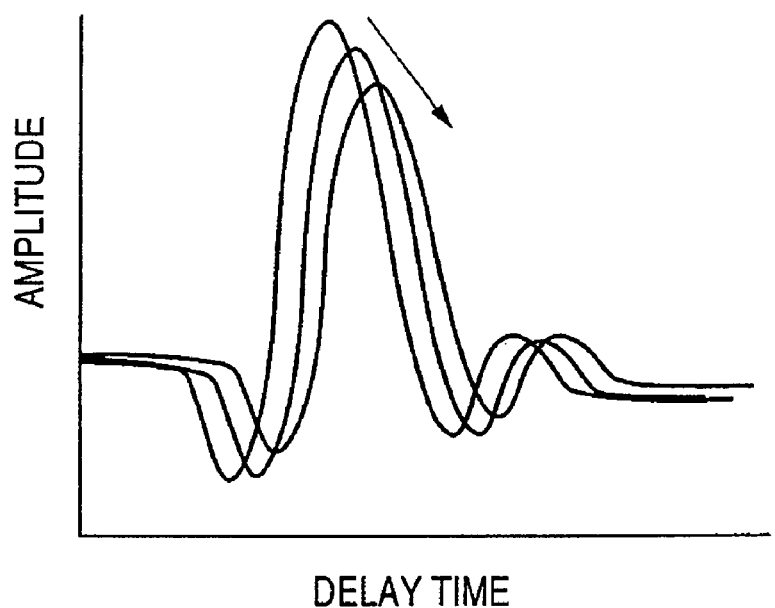
FIGS. 3A and 3B are views describing an example of a sensing signal in the inspection apparatus of the present invention.
Figure 3B:
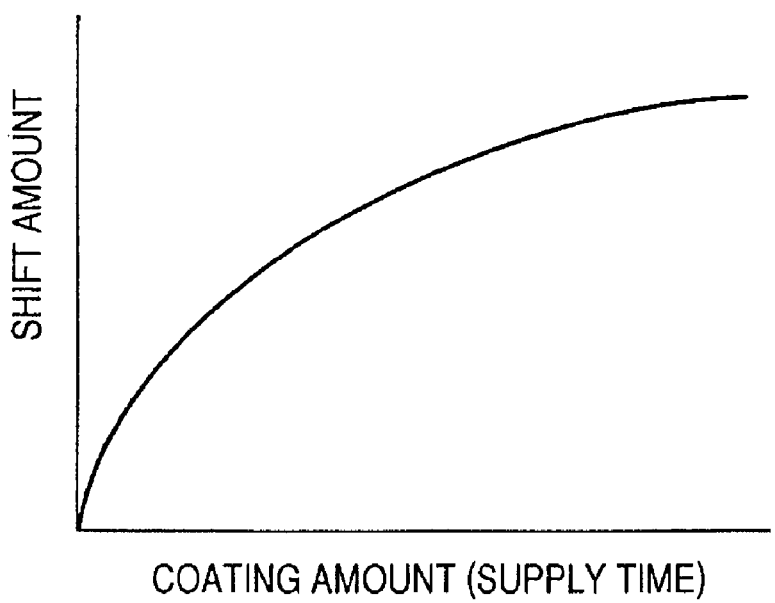

When a propagating terahertz wave is measured while depositing the inspection object 16 in this way from the instance where the inspection object is not present, the detection pulse is changed in a direction indicated by the arrow as similarly illustrated in FIG. 3A, namely, in such a direction that the amplitude is low and the temporal delay is increased. When the supply time of the inspection object and the temporal shift amount of the detection pulse are plotted from the start of the coating of the inspection object, a state illustrated in FIG. 3B is obtained, and it tends to be saturated at a certain time. In a case where the concentration of the solution of the inspection object or the applied electric field between the capillary electrode 17 and the signal line 3 are constant, the rate of this shift varies depending on the conditions of the avidin, namely, depending on whether it is in a normal state or it receives a thermal denaturation. Thus, this denaturation can be detected. On the other hand, even in the case of the same avidin, the coating speed varies depending on the concentration, and the rate of the shift is changed, thereby enabling an unknown avidin solution to be known for its concentration. When this is prepared as a database in advance, the absolute amount of the avidin can be also known.

Figure 4:
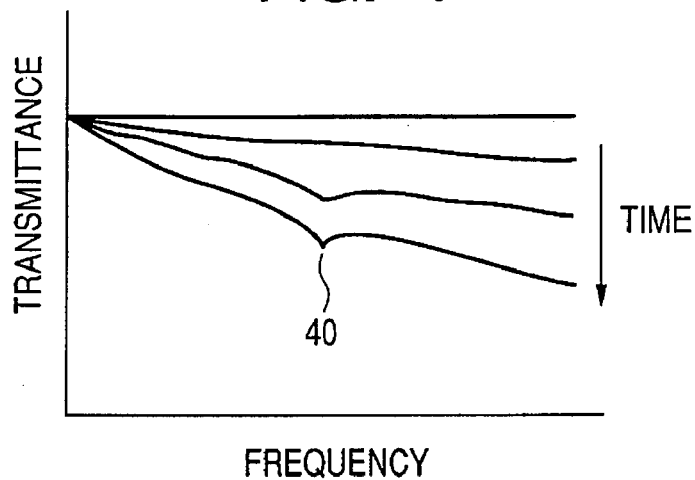
FIG. 4 is a view describing an example of a spectrum in the inspection apparatus of the present invention.

Similarly, if the database of various kinds of living organism related molecules is obtained, an inspection object can be analyzed in accordance with the shift amount and the amplitude attenuation amount. Further, in the inspection object (cytosine or the like) which exhibits a characteristic absorption spectrum 40 as illustrated in FIG. 4, the temporal change is observed for a frequency spectrum of a transmittance of a terahertz wave with respect to the deposited inspection object. Then, the absorption is increased according to the inspection object coating amount, and the absorption spectrum is obviously recognized.

When the analysis method of measuring such temporal change is used, the coating of the inspection object may be stopped at the saturation point or when the difference has been detected, thereby enabling the inspection of the inspection object with as small an amount as possible. Further, it is possible to carry out the quantitative evaluation with high stability and reliability. At this time, in order to stabilize the drying state of the inspection object, the evaluation may be carried out inside a box for controlling humidity.

In a case where the inspection object molecule to be applied by the above-mentioned method has the electric polarization in a certain direction, when the inspection object is deposited on the signal line 3 by the electrostatic force, the directions of the polarizations can be aligned, thereby maintaining the orientation. In this case, the interaction between the terahertz wave propagating through the transmission line and the inspection object are made strong, which provides the effect of improving the sensibility of the inspection.

Second Example

Figure 5:
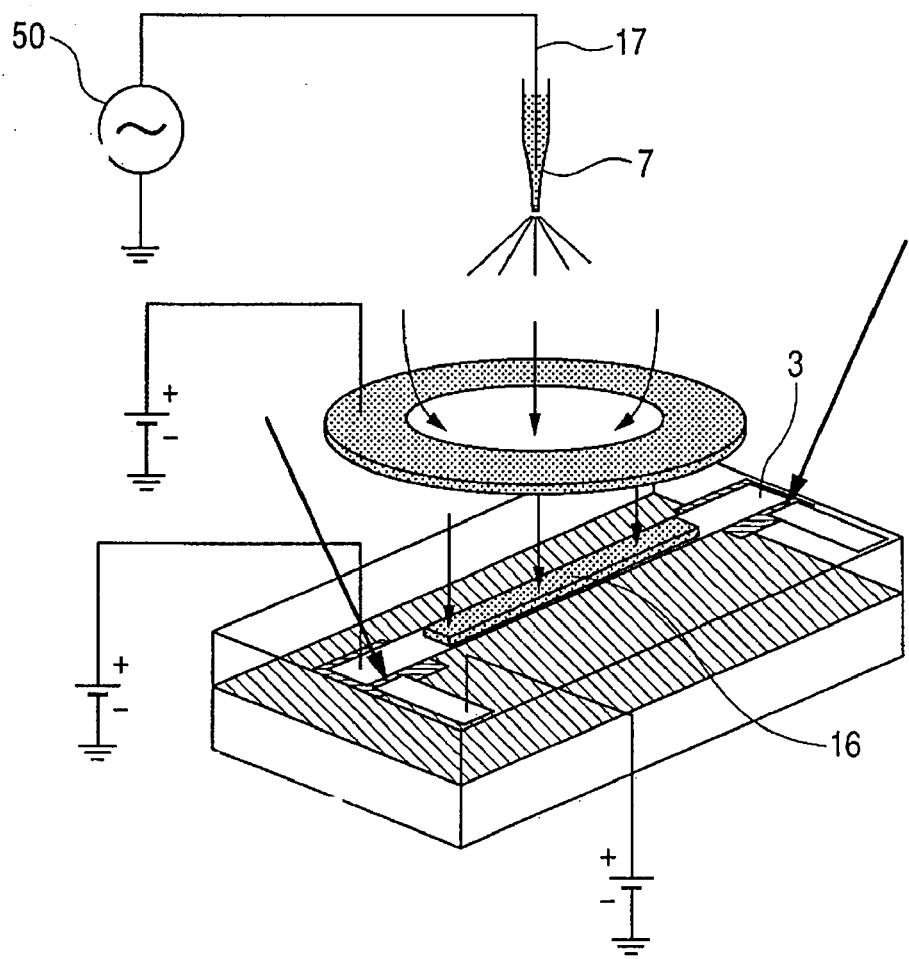
FIG. 5 is a perspective view of an inspection apparatus that uses a transmission line (micro strip) type sensor according to a second example.

FIG. 5 illustrates a second example according to the present invention. A sensor chip 20 and an inspection object coating apparatus 21 are similar to those of the first example, and the feature of the second example lies in the drive method. In FIG. 5, reference numerals of portions identical with those of FIG. 1 are omitted except some of them.

In this example, an electrode 17 for applying a voltage to a capillary 7 is connected to a power source 50 that can be modulated. With regard to the modulation, for example, the drive is conducted such that a signal of 100 Hz at ±200 V is superimposed on the electrostatic field caused by an application voltage of 3 kV. In this case, the modulation of the coating amount of an inspection object molecules 16 onto the signal line 3 that is a conductive region is executed. Thus, when on the detection side the synchronous detection is conducted with respect to 100 Hz, it is possible to remove noise components caused by the drift preliminarily possessed by the transmission line type sensor.

As a result, when obtaining the temporal changes in the delay time shift and peak amplitude change of the pulse signal as described with reference to FIG. 3A, the precision thereof can be improved.

Third Example

Figure 6:
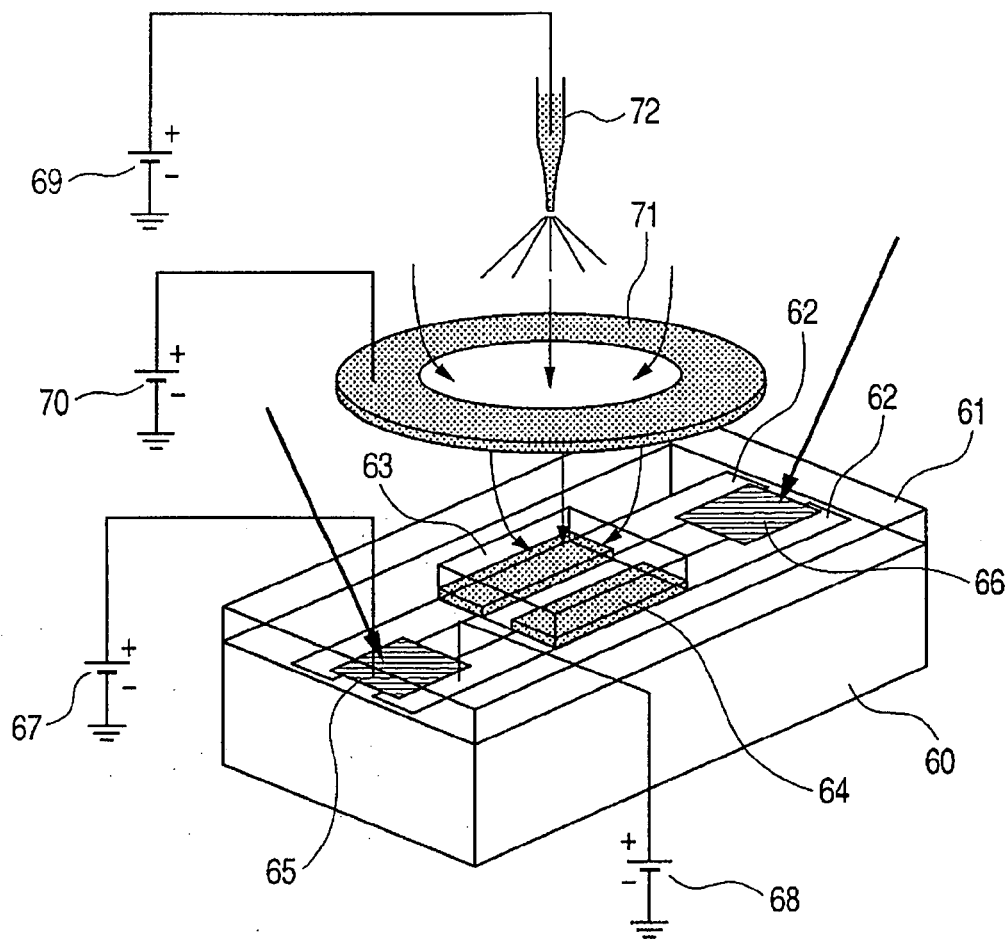
FIG. 6 is a perspective view of an inspection apparatus that uses a transmission line (coplanar strip line) type sensor according to a third example.
Figure 7:
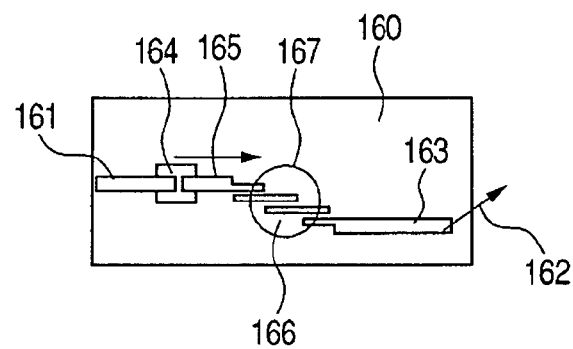
FIG. 7 is a view describing a conventional technique.

A third example according to the present invention is that applied to a coplanar strip line as shown in FIG. 6. In FIG. 6, a line 62 including two Ti/Au electrodes having a width of 10 µm and an interval of 16 µm is formed on a quartz substrate 60, and a BCB 16 serving as a dielectric is further formed on the surface thereof. LT-GaAs thin films 65 and 66 are transferred similarly to the first example, but in this example, they are bonded on top surfaces of the lines 62 so as to stride over the two lines 62. A region 63 on which the inspection object is to be deposited is formed on the BCB 61 formed on the surface, and the BCB 61 has a window opened from which the electrode 62 is exposed. Further, in each of the electrodes 62, a region (not shown) for connecting power sources 67 and 68 are formed by providing a window thereon. The BCB 16 of the dielectric can be omitted, although such omission may cause slightly inaccurate formation of the region of the line 62 where the inspection object is to be deposited.

Even in the chip of this example, in accordance with the controls of the power sources 67 and 68, a DC voltage of 10 V is applied between the two lines 62, and a terahertz pulse is generated by applying a laser beam in the similar manner as in the above-mentioned example. The detector side of the GaAs thin film 66 has such a circuit configuration that in order to cut the DC voltage applied on the generation side, only a high frequency signal component is detected through a high pass filter (not shown).

With regard to the coating of an inspection object 64, controlling is carried out by the electric field between a power source 69 of a capillary portion 72 and the signal line 62, similarly to the first example. However, since a high voltage of about 3 kV is applied, the potential difference of 10 V between the power source 67 and the power source 68 has no substantial influence on the spraying of the inspection object. Further, in the configuration of FIG. 6, because of the BCB 16 formed on the surface, the inspection object is hardly applied on any region except a window 63. As a matter of course, a collimator electrode 71 to which a voltage of about 0.5 kV is applied from a power source 70 contributes to this fact.

In this example, a plasmid DNA of 54 k bases is applied. At this time, as compared with normal ones with a double chain, the one having a single chain generated by thermal dissociation tends to show a large temporal change in the shift amount for the same concentration of 1 µg/µl. Thus, the difference between the structures can be analyzed. When this effect is used in a certain particular pathology diagnosis, a DNA having a complementary base sequence serving as a form is prepared and then a double chain is generated by the reaction of the thus prepared DNA with a sampled DNA, the existence of the sequence is revealed. For this reason, this can be used as a clinical diagnosis apparatus.

In the coplanar strip line 62 of this example, the leaking component of the electric field of the propagating terahertz wave to the surface becomes large. Thus, this example is characterized in that since the interaction between the inspection object 64 and the propagation terahertz wave becomes great, the sensibility becomes high, as compared with the case of the first example.

In the above-mentioned examples, the analysis example of the particular inspection object is described. When the database is established in advance, the present invention can be widely applied in analysis apparatus for the clinical diagnosis and inspection for proteins and DNA for medical use and in apparatus for purifying drugs or for analyzing action of drugs.

While the present invention has been described with reference to exemplary examples, it is to be understood that the invention is not limited to the disclosed exemplary examples. The scope of the following claims is to be accorded the broadest interpretation so as to encompass all such modifications and equivalent structures and functions.

This application claims the benefit of Japanese Patent Application No. 2006-125670, filed Apr. 28, 2006 which is hereby incorporated by reference herein in its entirety.

What is claimed is:

1. An inspection method of detecting an electromagnetic wave in a frequency range between 30 GHz and 30 THz which is propagated through a transmission line to obtain information on an inspection object deposited on a conductive region located in a site including at least a part of a range to which an electric field distribution of the electromagnetic wave propagating through the transmission line extends, comprising:

supplying the inspection object from an inspection object supply unit for holding and supplying the inspection object to an outside;

applying a voltage between the conductive region and an inspection object holding portion of the inspection object supply unit to generate an electric field;

guiding the supplied inspection object with an electrostatic force to deposit the object depositing selectively on the conductive region; and obtaining information on the inspection object by superimposing an alternating current component on the voltage to be applied to the inspection object holding portion of the inspection object supply unit to vary a rate of the deposition of the inspection object onto the conductive region, and carrying out a synchronous detection with this variation.

2. An inspection method according to claim 1, wherein information on the inspection object is obtained by obtaining a plurality of changes of a signal of the detected electromagnetic wave continuously or intermittently for an elapse of time, correspondingly to a temporal change of a deposition amount of the inspection object onto the conductive region.

3. An inspection method according to claim 2, further comprising stopping supply of the inspection object when a rate of the change of the signal of the detected electromagnetic wave becomes small with respect to the elapse of time or when the rate of the change is estimated to be small.

* * * * *